United States Patent
O'Flynn et al.

(10) Patent No.: US 10,173,053 B2
(45) Date of Patent: Jan. 8, 2019

(54) IMPLANTABLE MEDICAL DEVICE AND ASSEMBLY THEREOF

(71) Applicant: Cardiac Pacemakers, Inc., St. Paul, MN (US)

(72) Inventors: Alan James O'Flynn, Co. Tipperary (IE); Ray Burke, Cork (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 10 days.

(21) Appl. No.: 14/174,478

(22) Filed: Feb. 6, 2014

(65) Prior Publication Data

US 2014/0277234 A1    Sep. 18, 2014

Related U.S. Application Data

(60) Provisional application No. 61/777,473, filed on Mar. 12, 2013.

(51) Int. Cl.
| | |
|---|---|
| *A61N 1/00* | (2006.01) |
| *A61N 1/05* | (2006.01) |
| *A61N 1/365* | (2006.01) |
| *A61N 1/375* | (2006.01) |
| *H05K 1/02* | (2006.01) |
| *H05K 1/18* | (2006.01) |
| *H05K 3/28* | (2006.01) |
| *H05K 3/46* | (2006.01) |

(52) U.S. Cl.
CPC ........... *A61N 1/0587* (2013.01); *A61N 1/365* (2013.01); *A61N 1/3752* (2013.01); *H05K 1/185* (2013.01); *H05K 1/0231* (2013.01); *H05K 1/181* (2013.01); *H05K 3/284* (2013.01); *H05K 3/4697* (2013.01); *H05K 2201/10189* (2013.01); *H05K 2203/1316* (2013.01)

(58) Field of Classification Search
CPC ............................ A61N 1/3627; A61N 1/36521
USPC ...................................... 607/17, 119
See application file for complete search history.

(56) References Cited

U.S. PATENT DOCUMENTS

| | | | |
|---|---|---|---|
| 5,963,429 A * | 10/1999 | Chen | ............ H01L 25/0652 257/686 |
| 5,966,294 A | 10/1999 | Harada et al. | |
| 5,973,906 A | 10/1999 | Stevenson et al. | |
| 6,288,344 B1 | 9/2001 | Youker et al. | |
| 7,591,924 B2 | 9/2009 | Smith et al. | |

(Continued)

FOREIGN PATENT DOCUMENTS

| | | |
|---|---|---|
| CN | 105246545 A | 1/2016 |
| CN | 105246545 B | 1/2018 |

(Continued)

OTHER PUBLICATIONS

"International Application Serial No. PCT/US2014/015107, International Search Report dated Apr. 4, 2014", 5 pgs.

(Continued)

*Primary Examiner* — Nadia A Mahmood
(74) *Attorney, Agent, or Firm* — Schwegman Lundberg & Woessner, P.A.

(57) ABSTRACT

This document describes an apparatus including an implantable medical device having a printed circuit board. The apparatus can include a connector block for a lead terminal of the implantable medical device mounted directly to the printed circuit board.

20 Claims, 4 Drawing Sheets

(56) References Cited

U.S. PATENT DOCUMENTS

| | | | |
|---|---|---|---|
| 2006/0089682 A1 | | 4/2006 | Kronich et al. |
| 2010/0016928 A1* | | 1/2010 | Zdeblick .................. A61N 1/05 607/72 |

FOREIGN PATENT DOCUMENTS

| | | |
|---|---|---|
| EP | 0587379 A2 | 3/1994 |
| EP | 2529790 A1 | 12/2012 |
| JP | 2011517970 A | 6/2011 |
| JP | 2016510631 A | 4/2016 |
| WO | WO-1989005170 A1 | 6/1989 |
| WO | WO-0232503 A1 | 4/2002 |
| WO | WO-2002032503 A1 | 4/2002 |
| WO | WO-2004052457 A1 | 6/2004 |
| WO | WO-2013162726 A1 | 10/2013 |
| WO | WO-2014143460 A1 | 9/2014 |

OTHER PUBLICATIONS

"International Application Serial No. PCT/US2014/015107, Written Opinion dated Apr. 4, 2014", 6 pgs.

"International Application Serial No. PCT/US2014/015107, International Preliminary Report on Patentability dated Sep. 24, 2015", 8 pgs.

"Australian Application Serial No. 2014228643, Office Action dated Apr. 11, 2016", 2 pgs.

"Australian Application Serial No. 2014228643, Response filed Mar. 6, 2017 to Subsequent Examiners Report dated Jan. 18, 2017", 10 pgs.

"Australian Application Serial No. 2014228643, Response filed Dec. 20, 2016 to Office Action dated Apr. 11, 2016", 17 pgs.

"Australian Application Serial No. 2014228643, Subsequent Examiners Report dated Jan. 18, 2017", 3 pgs.

"Australian Application Serial No. 2014228643, Subsequent Examiners Report dated Mar. 27, 2017", 6 pgs.

"Chinese Application Serial No. 201480014458.0, Office Action dated Mar. 2, 2017", w/ English Translation, 18 pgs.

"Chinese Application Serial No. 201480014458.0, Office Action dated Jul. 15, 2016", With English Translation, 19 pgs.

"Chinese Application Serial No. 201480014458.0, Response filed Nov. 25, 2016 to Office Action dated Jul. 15, 2016", With English claims, 12 pgs.

"Japanese Application Serial No. 2016-500210, Response filed Nov. 22, 2016 to Office Action dated Aug. 23, 2016", With English claims, 11 pgs.

Stevenson, Robert A, "Design and application of broadband ceramic feedthrough capacitor EMI filters to cardiac pacemakers and implantable defibrillators", Engineering in Medicine and Biology Society, Proceedings of the 19th International Conference of the IEEE., (1997), 2558-2562.

"Australian Application Serial No. 2014228643, Response filed Apr. 4, 2017 to Subsequent Examiners Report dated Mar. 27, 2017", 10 pgs.

"Australian Application Serial No. 2014228643, Subsequent Examiners Report dated Apr. 10, 2017", 5 pgs.

"Chinese Application Serial No. 201480014458.0, Office Action dated Jul. 18, 2017", w/ English summary from agent's letter, 4 pgs.

"Chinese Application Serial No. 201480014458.0, Response filed May 15, 2017 to Office Action dated Mar. 2, 2017", w/ claims in English, 12 pgs.

"European Application Serial No. , Response filed Jan. 12, 2016 to Communication Pursuant to Rules 161(1) and 162 EPC dated Oct. 27, 2015", 18 pgs.

"Japanese Application Serial No. 2016-500210, Examiners Decision of Final Refusal dated Apr. 25, 2017", w/ English summary, 7 pgs.

"Australian Application Serial No. 2017202387, First Examination Report dated Sep. 21, 2017", 3 pgs.

"Australian Application Serial No. 2017202387, Response filed Apr. 18, 2018 to First Examination Report dated Sep. 21, 2017", 13 pgs.

"Australian Application Serial No. 2017202387, Subsequent Examiners Report dated May 22, 2018", 5 pgs.

"Chinese Application Serial No. 201480014458.0, Response filed Sep. 7, 2017 to Office Action dated Jul. 18, 2017", w/ claims in English, 31 pgs.

"European Application Serial No. 14706410.9, Communication Pursuant to Article 94(3) EPC dated Jun. 30, 2017", 4 pgs.

"European Application Serial No. 14706410.9, Response filed Aug. 30, 2017 to Communication Pursuant to Article 94(3) EPC dated Jun. 30, 2017", claims not amended at this time, 4 pgs.

"Japanese Application Serial No. 2016-500210, Appeal of an Adverse Decision filed Aug. 23, 2017 to Examiners Decision of Final Refusal dated Apr. 25, 2017", w/ claims in English, 16 pgs.

\* cited by examiner

IMPLANTABLE MEDICAL DEVICE AND ASSEMBLY THEREOF

CLAIM OF PRIORITY

This application claims the benefit of priority under U.S.C. § 119(e) of U.S. Provisional Patent Application Ser. No. 61/777,473, filed on Mar. 12, 2013, which is herein incorporated by reference in its entirety.

BACKGROUND

A pulse generator (implantable medical device or IMD), such as a cardiac rhythm management device, can include a filter capacitor. The filter capacitor is attached as a separate electronic component. For example, the filter capacitor may be coupled to a feed-through terminal pin assembly having one or more conductive terminal pins supported by an insulator structure. The conductive terminal pins are coupled to a connector block at one end thereof and to a printed circuit board at other end. Some of these electronic components, i.e., the printed circuit board and the filter capacitor, along with a power source (battery) are further hermetically sealed within a casing of a metallic biocompatible material.

A printed circuit board substrate including cavities in which electronic components, such as integrated circuits are mounted and encapsulated is discussed in U.S. Pat. No. 5,963,429 entitled PRINTED CIRCUIT SUBSTRATE WITH CAVITIES FOR ENCAPSULATING INTEGRATED CIRCUITS.

An implantable integrated circuit structure comprising a conformal thin-film sealing layer for hermetically sealing circuitry layers is discussed in U.S. Publication No. 20100016928, abandoned, entitled VOID-FREE IMPLANTABLE HERMETICALLY SEALED STRUCTURES.

Overview

The above-mentioned approaches for assembling electronic components to form an IMD involves various steps of manufacturing processes that make the entire assembling process of the IMD complex, time consuming, and costly. Additionally, such an IMD includes limited capabilities to their use in more demanding environments where moisture and other contaminants are prevalent. Therefore, there is a need for an IMD and/or a method of assembling components for an IMD, which is simple and can be used in demanding environments.

By way of an example, this document describes saving steps of manufacturing processes by precluding use of conductive terminal pins and a separate filter capacitor. Also, the document describes providing a hermetic sealing for the IMD that can be capable of being used in demanding environments and that can help in saving in expensive component packaging and shielding measures.

In an example, this document describes an apparatus such as a cardiac rhythm management device including an implantable medical device having a printed circuit board. The apparatus includes a connector block for a lead terminal of the implantable medical device mounted directly to the printed circuit board.

In an example, this document describes an apparatus such as a cardiac rhythm management device including an implantable medical device having a printed circuit board. The apparatus includes a connector block for a lead terminal of the implantable medical device mounted directly to the printed circuit board. The apparatus includes a filter capacitor located within a body of the printed circuit board and located beneath the connector block. The connector block and the printed circuit board are encapsulated within an overmolded polymer material.

In an example, this document describes a method for assembling an implantable medical device. The method can include connecting a connector block for a lead terminal of the implantable medical device directly to a printed circuit board. The method includes providing a filter capacitor within a body of the printed circuit board and beneath the connector block. The method can include encapsulating the connector block and the printed circuit board with an overmolded polymer material.

BRIEF DESCRIPTION OF THE FIGURES

The drawings illustrate generally, by way of an example, but not by a way of limitation, various embodiments discussed in the present document.

DETAILED DESCRIPTION

Figure 1:
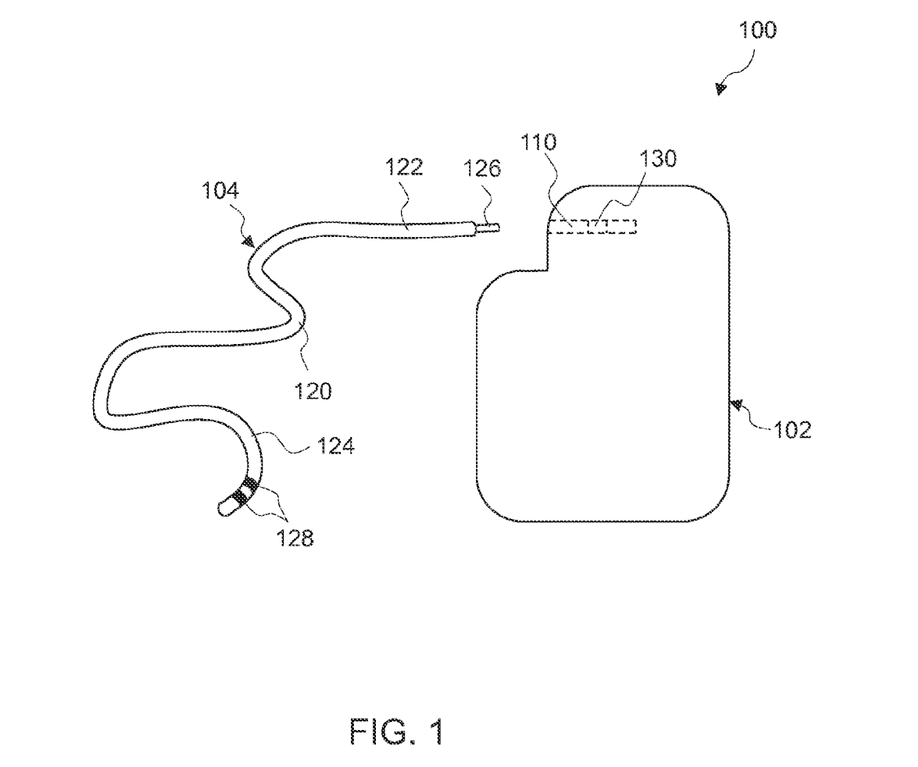
FIG. 1 illustrates a schematic diagram of an apparatus having an implantable medical device and an implantable lead, according to an example.

FIG. 1 shows an example of an apparatus 100 having an implantable medical device (IMD) 102 and an implantable lead 104. In one embodiment, the IMD 102 can be an implantable pulse generator adapted to generate electrical signals to be delivered to a target tissue for pacing, and/or sensing electrical activity of the target tissue. For example, the IMD 102 shown in FIG. 1 can be a pulse generator adapted to deliver electrical stimulation or sense electrical activity to/from a heart (not shown) and may be implanted subcutaneously within the patient's chest or abdomen.

The IMD 102 can include a port 110 for providing electrical and mechanical connection between the IMD 102 and the implantable lead 104. The IMD 102 can be connected to the implantable lead 104 to convey electrical signals between the IMD 102 and the heart. The implantable lead 104 may be implanted through the patient's vascular system (not shown), such as a vascular entry site formed in the wall of the left subclavian vein, and at least a portion of the implantable lead 104 may be secured by suturing to subcutaneous tissue.

The implantable lead 104 can include a flexible lead body 120 having a proximal end portion 122 and a distal end portion 124. The proximal end portion 122 can be configured to have a lead terminal 126 that can facilitate in establishing the electrical and mechanical connection between the IMD 102 and the implantable lead 104. The implantable lead 104 can include a plurality of conductor wires (not shown) disposed within a plurality of conductor lumens extending axially within the lead body 120 from the proximal end portion 122 to the distal end portion 124. The implantable lead 104 can also include a plurality of electrodes 128 (or defibrillation coils) mechanically coupled to the distal end portion 124 of the lead body 120. The electrodes 128 and the lead terminal 126 can be electrically coupled by the conductor wires disposed within the plurality of conductor lumens.

It may be evident that the apparatus 100 may include one or more implantable leads similar to the implantable lead 104, and accordingly the IMD 102 may include one or more ports for providing electrical and mechanical connection there-between. The port 110 can be configured to comply with a voltage standard, such as DF-4 standard (high voltage), IS-4 standard (low voltage), and IS-1 (low voltage) standard. Similarly, the implantable lead 104 can be configured to comply with a corresponding port's voltage, such as DF-4 standard (high voltage), IS-4 standard (low voltage), and IS-1 (low voltage) standard.

The apparatus 100 can include a connector block 130 disposed within the port 110 of the IMD 102. The port 110 can provide an access to the connector block 130 for the lead terminal 126 of the implantable lead 104. The lead terminal 126 can be sized to be inserted into and received by the connector block 130 disposed within the port 110. The connector block 130 is explained in greater detail in conjunction with later figures.

Figure 2:
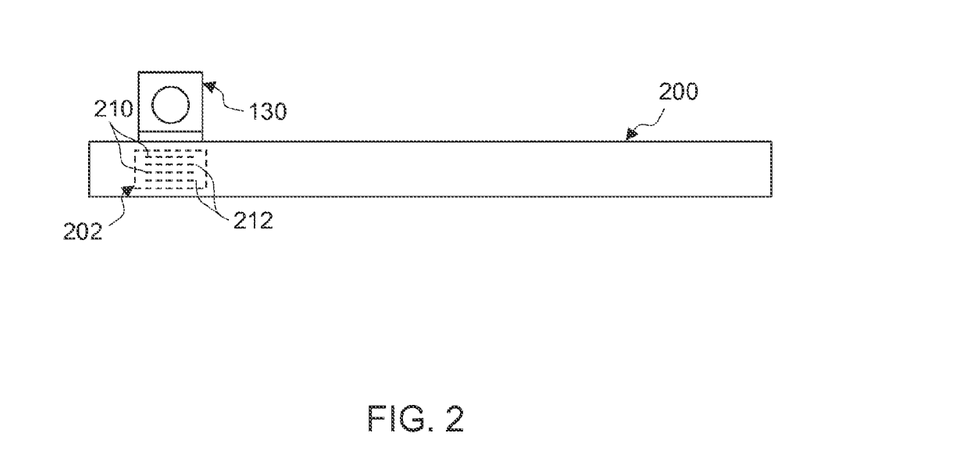
FIG. 2 illustrates a schematic diagram of a printed circuit board of the implantable medical device, according to an example.

FIG. 2 shows an example of a printed circuit board (PCB) 200 for the IMD 102. The PCB 200 can be a fiber board, for example. The PCB 200 can be made of a substrate material, such as, FR-4 (epoxy E-glass). The PCB 200 can include conductor traces applied on the substrate material to form a desired pattern based on a circuit design. The conducting traces may be formed on the substrate material by chemical deposition, etching, lithography, spray deposition, cutting, and the like.

The apparatus 100 can include a filter capacitor 202 located within a body (substrate material) of the PCB 200. The filter capacitor 202 can be located within the body of the PCB 200 and beneath the connector block 130. The filter capacitor 202 can be inserted into the PCB 200 during PCB manufacturing. In some embodiments, the filter capacitor 202 can be inserted within the PCB 200 using an encapsulated component placement (ECP) process. For example, the ECP process may be carried out with the help of the PCB 200, having two layers and at least one layer can be configured to have a cavity or a recess adapted to receive the filter capacitor 202 therein. The two layers of the PCB 200 can thereafter be thermally and/or mechanically pressed for embedding the filter capacitor 202 therewithin. Alternatively, during ECP process the filter capacitor 202 may be supported onto the PCB 200, and thereafter the filter capacitor 202 may be encapsulated with the substrate material of the PCB 200 by a suitable process, such as injection molding. The embedding of the filter capacitor 202 within the PCB 200 serves the purpose of protecting the filter capacitor 202 against environmental exposures.

In some embodiments, the filter capacitor 202 can include a plurality of plate layers, such as first and second plate layers 210 and 212, embedded within the body of the PCB 200. The first and second plate layers 210, 212 can be metalized ring or polygonal plate, sized and spaced apart from each other by a predetermined distance for defining a specific capacitance value of the filter capacitor 202. The filter capacitor 202 can include a dielectric material disposed between the first and second plate layers 210, 212.

The first plate layers 210 can be in conductive relation with each other, and further collectively in conductive relation with the connector block 130. For example, the first plate layers 210 may include a common output terminal in conductive relation with the conducting traces of the PCB 200 using a conductive polyimide fill or solder. The conducting traces of the PCB 200 can be further conductively coupled to the connector block 130. The second plate layers 212 can be in conductive relation with each other, and further collectively in conductive relation with a ground pin (not shown). For example, the second plate layer 212 can include a common output terminal conductively coupled to the ground pin using a conductive polyimide fill or solder.

In some embodiments, the PCB 200 can include a plurality of laminated layers (not shown), with at least one layer located above the filter capacitor 202 and at least one layer located beneath the capacitor. Due to the metalized nature of the first and second plate layers 210, 212, the filter capacitor 202 needs to be surrounded by the laminated layers. The laminated layers may be made of an insulative ceramic material. The filter capacitor 202 can help in decoupling/attenuating undesired interference signals of typically high frequency, such as EMI from cellular telephones or microwave ovens.

Figure 3:
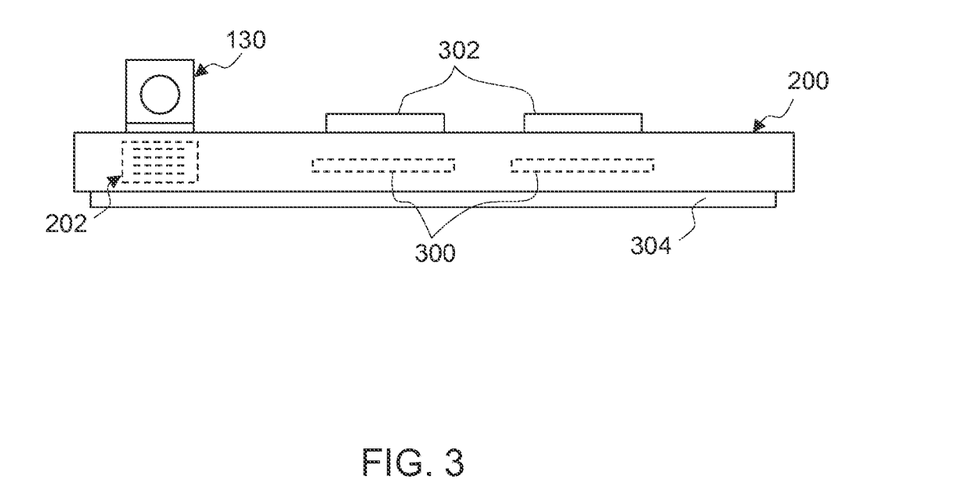
FIG. 3 illustrates the printed circuit board of FIG. 2 with various electronic components either mounted or inserted within the printed circuit board; according to an example.

FIG. 3 shows an example of the PCB 200 having various electronic components either mounted or inserted within the PCB 200. For example, the apparatus 100 can include electrically active or passive components adapted to perform signal analysis for providing electric therapy to a body of a patient. The IMD 102, having the PCB 200, can be used for providing cardiac therapy to the heart of the patient. In some embodiments, the IMD 102 can be implanted outside the heart and used for nerve stimulation, for example.

In an example, the PCB 200 can include one or more integrated circuits 300 embedded within the body of the PCB 200. As explained above, in an example, the PCB 200 can include two layers that sandwiches the filter capacitor 202 there-between. Similarly, the integrated circuits 300 can be embedded within the PCB 200. For example, the PCB 200 can include cavities or recesses adapted to receive the integrated circuits 300 therein, and with the thermal and/or mechanical press, the integrated circuits 300 can be embedded within the body of the PCB 200. In an example, the embedding of the integrated circuits 300 may happen during the manufacturing of the PCB 200. In an example, the integrated circuits 300 can include application specific integrated circuit (ASIC) chips. For example, one of the integrated circuits 300 may be an ASIC chip specifically designed for performing analysis of signals associated with the filter capacitor 202. The integrated circuits 300 may be conductively coupled to the conducting traces of the PCB 200 based on the circuit design.

As shown in FIG. 3, the apparatus 100 (shown in FIG. 1), particularly the IMD 102, can include one or more electronic components 302 mounted on the PCB 200. The electronic components 302 along with the integrated circuits 300 can be adapted to perform signal analysis for providing electric therapy to the patient's body. In an example, the electronic components 302 can include one or more diodes, amplifiers, transistors, oscillators, resistors, capacitors, inductors, transformers, RF transmitter/receiver, interconnects, and the like. The electronic components 302 can perform the intended one or more operations associated with the IMD 102. The electronic components 302 may be conductively coupled to the conducting traces of the PCB 200 based on the circuit design.

The apparatus 100, particularly the IMD 102, can include a power supply 304 coupled to the PCB 200. The power supply 304 can be a battery adapted to supply electrical power to the integrated circuits 300 and to the electronic components 302. In an example, the power supply 304 can be a lithium iodide-type battery. The power supply 304 can be conductively coupled to the conducting traces of the PCB 200 for supplying electrical power to the integrated circuits 300 and to the electronic components 302.

Figure 4:
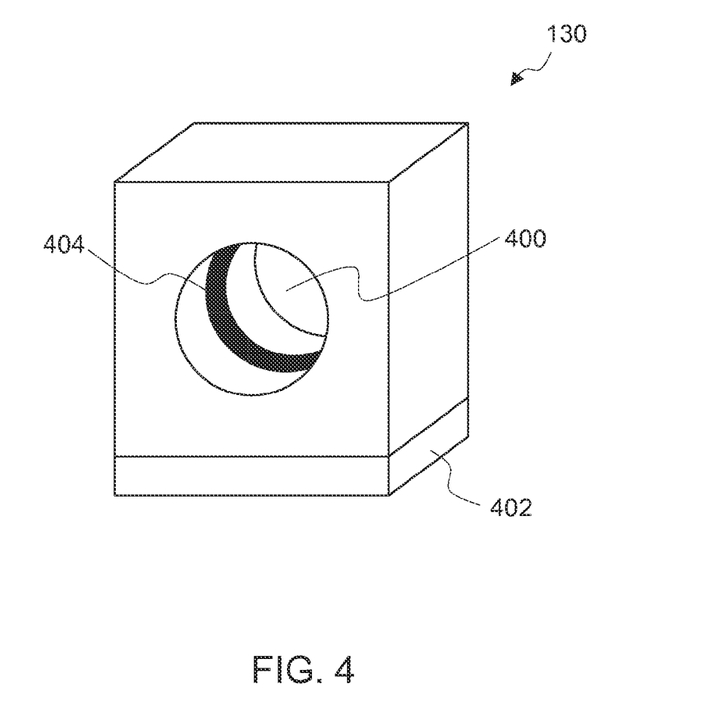
FIG. 4 illustrates a perspective diagram of a connector block mounted on the printed circuit board of FIGS. 2 and 3, according to an example.

FIG. 4 shows an example of the connector block 130 adapted to be mounted on the PCB 200 (shown in FIGS. 2-3). In an example, the connector block 130 can include a cuboidal structure having a through opening 400 sized to receive the lead terminal 126 (shown in FIG. 1) of the implantable lead 104 therein. The connector block 130 can include a rectangular cuboid structure or cylindrical structure having a through opening, such as the opening 400, configured to receive the lead terminal 126 therein. In an example, the connector block 130 can be made of metal to form a metallic housing.

The connector block 130 can be mounted directly onto the PCB 200. For example, the connector block 130 can include a gold plated plate 402, which may help in mounting the connector block 130 onto the PCB 200. The gold plated plate 402, at its one side, can be attached to the connector block 130 and, at the other side, can be attached to the PCB 200. For example, one side of the gold plated plate 402 can be spot welded to the metallic housing of the connector block 130 and the other side of the gold plated plate 402 can be soldered or spot welded to the conductive traces of the PCB 200. In an example, the side of the gold plated plate 402 that is spot welded to the metallic housing of the connector block 130 lacks gold (e.g., the gold can be removed) for better spot welding. However, the other side of the gold plated plate 402 that is soldered or spot welded to the PCB 200 can have gold. The substrate plate of the gold plated plate 402 can be a nickel-cobalt ferrous alloy or a Fe—Ni alloy, such as Kovar, for example.

The connector block 130 can include a contact spring 404 disposed within the metallic housing. For example, the connector block 130 can include an intermediate indented portion (not shown) adapted to receive the contact spring 404 therein. In an example, the contact spring 404 can be an electrically conductive flexible ring configured to contact a conductive portion of the lead terminal 126, when the lead terminal 126 is received within the opening 400 of the connector block 130. The contact spring 404 can facilitate in establishing electrical connection between the implantable lead 104 and the IMD 102. The contact spring 404 can be diametrically smaller as compared to the lead terminal 126 and due to the flexible nature of the contact spring 404; the contact spring 404 can help in holding the lead terminal 126 in place within the opening 400 and the port 110. Additionally, the lead terminal 126 can include a locking feature (e.g., structural configuration) that can help in mechanically locking the lead terminal 126 with the IMD 102. It may be evident that the apparatus 100 may include one or more such connector blocks similar to the block 130 disposed in the single port 110 for providing electrical and mechanical connection between the IMD 102 and the implantable lead 104.

Figure 5:
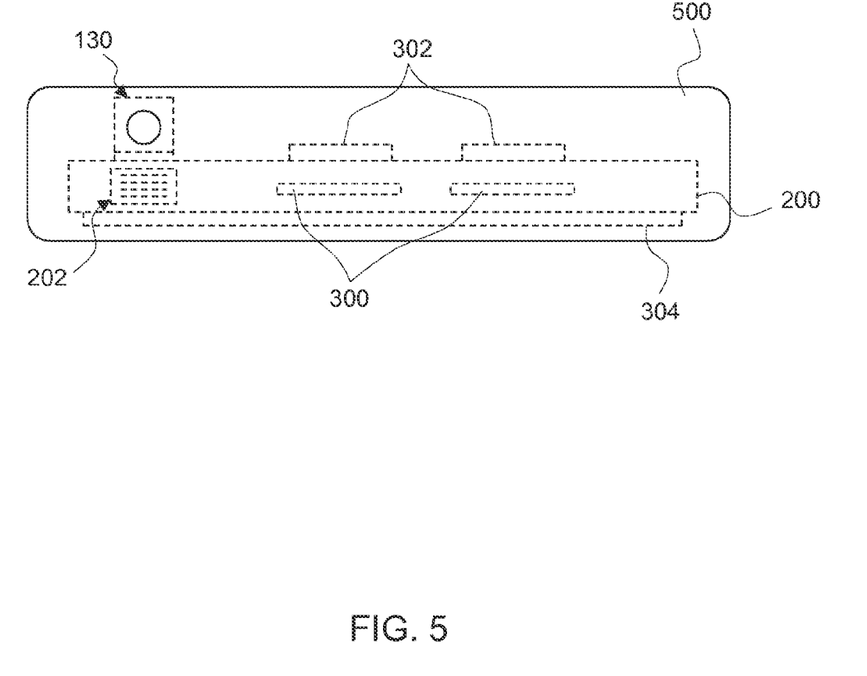
FIG. 5 is a schematic diagram of an implantable medical device encapsulated within an overmolded polymer material, according to an example.

FIG. 5 shows an example of the IMD 102 having a body 500. Specifically, the body 500 encapsulates the PCB 200, the connector block 130 mounted directly onto the PCB 200, the electronic components 302 mounted on the PCB 200, and the power supply 304 coupled to the PCB 200. The body 500 can be formed by an overmolded polymer material that provides hermetic sealing. The polymer material can include a biocompatible material, such as parylene, polytetrafluoroethylene, ethylene tetrafluoroethylene, polyimide, polyurethane, silicone, and aromatic polyester polymers, i.e. liquid crystal polymers. In an example, the polymer material can be injection molded, extruded or co-extruded instead of overmolding to form the encapsulated polymeric body 500 for the IMD 102.

It is to be understood that during encapsulation, the body 500 may be configured to have one or more ports, such as the port 110, to provide access to the connector block 130 for the lead terminal 126. The body 500 of the present disclosure can replace a typical bio compatible metal casing, such as a titanium casing, that hermetically seals a conventional IMD. The body 500 can be capable of providing hermetic sealing to the IMD 102. The body 500 can provide capabilities to the IMD 102 to be used in more demanding environments where moisture and other contaminants are prevalent.

In an example, prior to forming the body 500 by overmolding the polymer material, the PCB 200, the connector block 130, the electronic components 302 and the power supply 304 can be coated/sealed with a liquid crystal polymer using an injection molding process or any other process. Additionally, in an example, the apparatus 100 may include a moisture sensor for providing information pertaining to moisture accumulation/formation within the IMD 102 so as to take corrective measures against moisture accumulation/formation.

Figure 6:
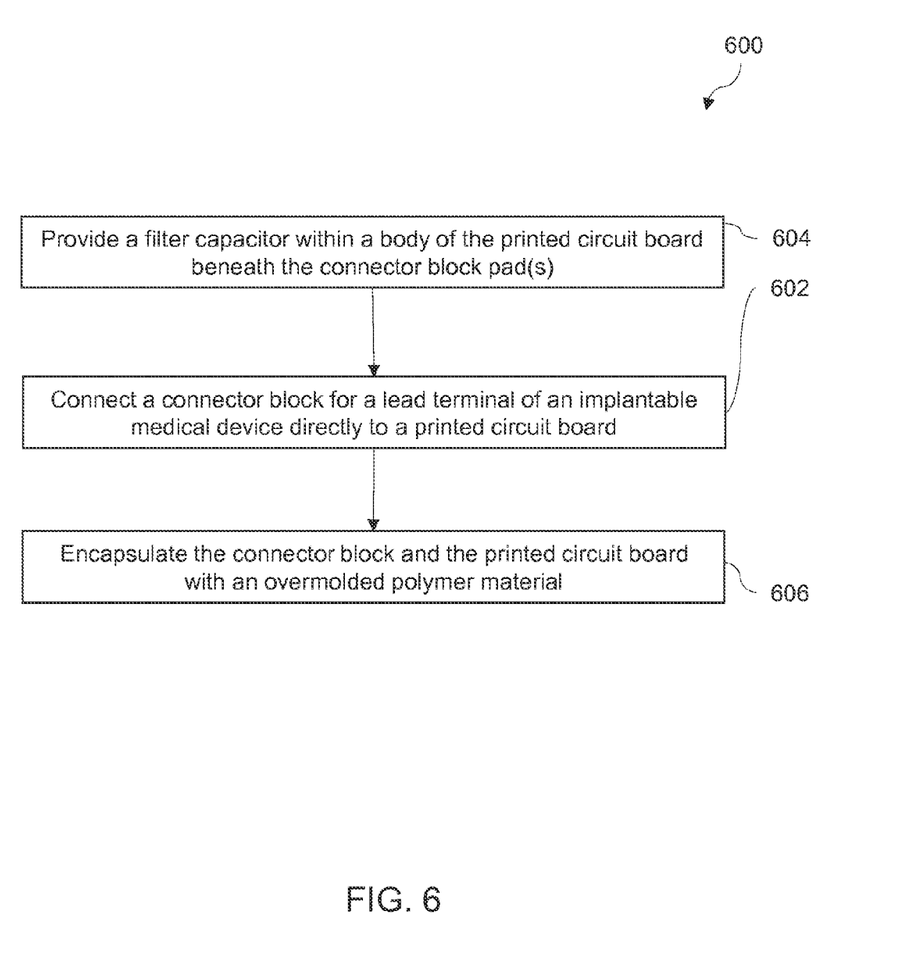
FIG. 6 is a flow diagram of a method for assembling an implantable medical device, according to an example.

FIG. 6 is a diagram of a method 600 for assembling an implantable medical device (IMD), such as the IMD 102.

At 604, a filter capacitor, such as the filter capacitor 202, can be provided within a body of a PCB. The filter capacitor can be inserted within the PCB during the time of PCB manufacture process. In some embodiments, the filter capacitor 202 may be inserted within the PCB 200 using an ECP process. For example, the PCB can include two layers with a cavity or recess adapted to receive the filter capacitor therein. The two layers of the PCB can be thereafter thermally and/or mechanically pressed for embedding the filter capacitor there-within. In addition to filter capacitor, one or more electronic elements, such as integrated circuits 300, may be embedded within the body of the PCB. Additionally, one or more electronic elements, such as the electronic components 302, for example, or one or more diodes, amplifiers, transistors, oscillators, resistors, capacitors, inductors, transformers, RF transmitter/receiver, or interconnects, can be directly mounted onto the PCB. The electronic components, either mounted on or received with the PCB, can perform signal analysis for providing electric therapy to a patient's body. The IMD can also include a power supply, such as a battery, adapted to supply electrical power to the electronic components for allowing the electronic component to perform one or more operations associated with the IMD.

At 602, a connector block, such as the connector block 130, for a lead terminal, such as the lead terminal 126, of the IMD can be mounted directly to the PCB 200. The filter capacitor 202 can be located beneath the connector block 130. The connector block can be a metallic cuboidal housing having a through opening, such as the opening 400. The opening 400 can be sized to receive therein the lead terminal of an implantable lead, such as the implantable lead 104, for establishing mechanical and electrical connection between the IMD and the implantable lead. In some embodiments, the connector block can be mounted directly onto the PCB with the help of a gold plated plate, such as the gold plated plate 402. For example, the gold plated plate on its one side can be spot welded to the connector block, and on its other side can be soldered or spot welded to the PCB.

At 606, the connector block and the printed circuit board can be encapsulated with an overmolded polymer material. Specifically, the PCB, the connector block and the electronic components mounted on the PCB, and the power supply coupled to the PCB can be encapsulated (e.g., hermetically sealed) within an overmolded polymer material. The polymer material may include biocompatible material, such as parylene, polytetrafluoroethylene, ethylene tetrafluoroethylene, polyimide, polyurethane, silicone, and aromatic polyester polymers, i.e. liquid crystal polymers. In some embodiment, the polymer material may be injection molded, extruded or co-extruded instead of overmolded to form an encapsulated body. It is to be understood that during encapsulation one or more ports, such as the port 110, can be provided for the lead terminal to access the connector block.

The apparatus 100 and the method 600 described herein can facilitate in reducing manufacturing process steps involved in an assembling process of an IMD. This can reduce the IMD manufacturing cost and time. For example, the apparatus 100 and the method 600 can preclude a need for a conventional feed-through terminal pin assembly, since a connector block can be directly mounted on the PCB. Further, a filter capacitor can be inserted within the PCB as an integral part of the PCB during manufacturing of the PCB, which can preclude a need for separately coupling a conventional filter capacitor with a conventional feed-through terminal pin assembly. Additionally, fewer electronic components can also be inserted within the PCB giving more available free surface area for additional electronic components to be mounted onto the PCB. Moreover, inserting the electronic components within the PCB provides compact design (miniaturization) for the IMD. This can improve electrical and thermal performance of the electronic components. This can help in saving in expensive component packaging and shielding measures, and can help in reducing PCB complexities.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. The above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus comprising:
   an implantable medical device including a printed circuit board;
   an implantable lead having a distal portion having an electrode and a proximal portion having a lead terminal; and
   a connector block for directly connecting to the lead terminal of the implantable lead, the connector block being located directly on and mounted directly on a surface of the printed circuit board.

2. The apparatus of claim 1, including a filter capacitor located within a body of the printed circuit board and located beneath the connector block.

3. The apparatus of claim 2, wherein the filter capacitor includes a plurality of plate layers embedded within the body of the printed circuit board.

4. The apparatus of claim 2, wherein the printed circuit board includes a plurality of laminated layers, with at least one layer located above the filter capacitor and at least one layer located beneath the capacitor.

5. The apparatus of claim 1, wherein the connector block includes a gold plated plate attached to one side which is soldered or spot welded to the printed circuit board.

6. The apparatus of claim 1, wherein the printed circuit board further includes one or more integrated circuits embedded within the body of the circuit board.

7. The apparatus of claim 1, further including one or more electronic components coupled to the printed circuit board and configured to perform signal analysis for providing electric therapy to a body, and further including a power supply coupled to the printed circuit board.

8. The apparatus of claim 7, wherein the connector block, the printed circuit board, the one or more electronic components, and the power supply are encapsulated within an overmolded polymer material.

9. The apparatus of claim 8, including one or more ports within the overmolded polymer material to provide access to the connector block for the lead terminal.

10. The apparatus of claim 1, wherein the connector block includes a metallic housing and a contact spring within the housing for receiving the lead terminal.

11. An apparatus comprising:
an implantable medical device including a printed circuit board;
an implantable lead having a distal portion having an electrode and a proximal portion having a lead terminal;
a connector block for directly connecting to the lead terminal of the implantable lead, the connector block being located directly on and mounted directly on a surface of the printed circuit board;
a filter capacitor located within a body of the printed circuit board and located beneath the connector block; and
wherein the connector block and the printed circuit board are encapsulated within an overmolded polymer material.

12. The apparatus of claim 11, wherein the filter capacitor includes a plurality of plate layers embedded within the body of the printed circuit board.

13. The apparatus of claim 11, wherein the printed circuit board includes a plurality of laminated layers, with at least one layer located above the filter capacitor and at least one layer located beneath the capacitor.

14. The apparatus of claim 11, wherein the connector block includes a gold plated plate attached to one side which is soldered or spot welded to the printed circuit board.

15. The apparatus of claim 11, wherein the printed circuit board further includes one or more integrated circuits embedded within the body of the circuit board.

16. The apparatus of claim 11, further including one or more electronic components coupled to the printed circuit board and configured to perform signal analysis for providing electric therapy to a body, and further including a power supply coupled to the printed circuit board.

17. A method comprising:
providing an implantable lead having a distal portion having an electrode and a proximal portion having a lead terminal;
locating and connecting a connector block directly on a surface of a printed circuit board, the connector block for directly connecting to the lead terminal of the implantable lead;
providing a filter capacitor within a body of the printed circuit board and beneath the connector block; and
encapsulating the connector block and the printed circuit board with an overmolded polymer material.

18. The method of claim 17, wherein connecting the connector block includes connecting a gold plated plate on the connector block to a trace of the printed circuit board.

19. The method of claim 17, wherein the filter capacitor is embedded within the body of the printed circuit board.

20. The method of claim 19, wherein the printed circuit board includes a plurality of laminated layers, with at least one layer located above the filter capacitor and at least one layer located beneath the capacitor.

* * * * *